United States Patent [19]

Noda et al.

[11] Patent Number: 5,521,157

[45] Date of Patent: May 28, 1996

[54] MODIFIED POLYPEPTIDE COMPOUND WITH VIP-LIKE ACTIVITY

[75] Inventors: Hitoshi Noda; Hidehumi Yamakawa; Shigeaki Yoshina; Tsutomu Ishida; Noboru Tomiya, all of Aichi, Japan

[73] Assignee: Sanwa Kagaku Kenkyusho Co., Ltd., Nagoya, Japan

[21] Appl. No.: 361,443

[22] Filed: Dec. 20, 1994

[30] Foreign Application Priority Data

Dec. 20, 1993 [JP] Japan ..................... 5-319815

[51] Int. Cl.⁶ ................. A61K 38/00; A61K 38/02; C07K 5/00; C07K 7/00
[52] U.S. Cl. ............... 514/12; 530/345; 530/300; 530/308; 530/324
[58] Field of Search ................. 530/324, 345, 530/300, 308; 514/12

[56] References Cited

FOREIGN PATENT DOCUMENTS

| 0463450 | 1/1992 | European Pat. Off. .......... C07K 7/10 |
| 0613904 | 9/1994 | European Pat. Off. .......... C07K 7/10 |

OTHER PUBLICATIONS

Horn, M. J. and Laursen, R. A. FEBS Lett., 36, 285–288 (1973).
Kempe, T. et al., Biotechnology, 4, 566–568 (1986).

Primary Examiner—Christina Y. Chan
Assistant Examiner—A. M. Davenport
Attorney, Agent, or Firm—Sughrue, Mion, Zinn, Macpeak & Seas

[57] ABSTRACT

The modified polypeptide compound of the present invention is represented by the following general formula ((SEQ ID NO: 2)-X):

His-Ser-Asp-Ala-Val-Phe-Thr-Gly-Asn-Tyr-Thr-Lys-Leu-Arg-Lys-Gln-Leu-Ala-Ala-Lys-Lys-Tyr-Leu-$R^1$-Lys-Ala-Leu-$R^2$-Hse-X wherein $R^1$ represents an Asn, Lys or Gln residue, $R^2$ represents a Lys or Arg residue, Hse represents a homoserine residue, and X represents $NHR^3$ or $NR^4R^5$, wherein $R^3$ represents a hydrocarbon residue having 18 or less carbon atoms or a polyalkylamine having 2 or more amino groups in its molecule, or $R^4$ and $R^5$ represent hydrocarbon residues, provided that the total carbon number of $R^4$ and $R^5$ is 18 or less. This modified polypeptide compound has a strong activity as a smooth muscle relaxant, and has excellent stability and prolonged duration of action. These characteristics make it suitable as an active ingredient in a drug for preventing and treating bronchial asthma and impotence.

5 Claims, No Drawings

MODIFIED POLYPEPTIDE COMPOUND WITH VIP-LIKE ACTIVITY

FIELD OF THE INVENTION

This invention relates to a novel modified polypeptide compound and the use of the same.

The modified polypeptide compound according to the present invention shows a strong smooth muscle relaxant activity, a high stability, and a good persistence. Thus, it is usable as the active ingredient in a drug for preventing and treating bronchial asthma and impotence.

BACKGROUND OF THE INVENTION

A number of polypeptides having smooth muscle relaxant activity have been discovered. VIP (vasoactive intestinal polypeptide) is an example of such polypeptides. VIP is a peptide hormone that was purified from a side fraction in the extraction and purification of secretin from porcine duodenum in 1970 by Said and Mutt. The primary amino acid structure of VIP, which was clarified in 1974 (*Eur. J. Biochem.*, vol. 42, pp. 581–589 (1974)), is as follows (SEQ ID NO: 1):

(SEQ ID NO: 1):
```
    1                           5
 Hi—Ser—Asp—Ala—Val—Phe—Thr—Asp—
   10                          15
 Asn—Tyr—Thr—Arg—Leu—Arg—Lys—Gln—
                 20
 Met—Ala—Val—Lys—Lys—Tyr—Leu—Asn—
   25      28
 Ser—Ile—Leu—Asn—NH_2
```

Since this amino acid structure is similar to those of secretin and glucagon, VIP is considered to be a peptide hormone belonging to the glucagon-secretin family.

VIP occurs widely in the nervous system, as well as in the digestive tract, and has various biological activities. It is clear that VIP has strong vasodilating and hypotensive activity, smooth muscle relaxant activity, intestinal juice secretion promoting activity, pancreatic juice and bile secretion promoting activity, gastric juice secretion suppressing activity, and glycogenolitic promoting activity. Although the presence of VIP in the lungs of normal subjects has been confirmed, this polypeptide has never been found in patients with bronchial asthma (*N. Eng. J. Med.*, vol. 320, pp. 1244–1248 (1989)).

Based on these facts, it is expected that VIP is applicable to the treatment of, in particular, bronchial asthma from among the various actions as described above. In fact, it is reported that the administration of natural type VIP, which has the amino acid sequence of human VIP, to man exhibits, although slightly, a suppressive effect on tracheostenosis induced by histamine (*Pharmacologist*, vol. 25, pp. 123 (1983); and *Am. Rev. Respir. Dis*, vol. 130, pp. 162–166 (1984)).

Natural type VIP, however, is highly unstable under the conditions usually employed for storing drugs. Furthermore, it has been demonstrated that when natural VIP is administered into, for example, the respiratory tract, it is easily degraded by protease. It is reported that, when natural type VIP is incubated together with enkephalinase, which is an enzyme frequently observed on the respiratory tract mucosa, in an in vitro test, more than 70% of the VIP is degraded within 15 minutes (*Biochem. Biophys. Res. Commun.*, vol. 158, pp. 850–854 (1989)). It is also reported that when VIP is treated with a broncho-alveolar lavage wash from guinea pig at 37° C., the half-life of VIP is about 1.5 hours (*Biomedical Res.*, vol. 13, Supplement 2, pp. 25–30 (1992)).

Workers at the Applicants' company have previously found that a compound having an amino acid residue other than a methionine residue at the 17-position and a homoserine residue (Hse, including homoserine lactone residues) at the C-terminal as well as an amide derivative and a higher fatty acid amide derivative thereof show VIP-like physiological activities (JP-A-4-59794 and EP-A-0,463,450; the term "JP-A" as used herein means an "unexamined published Japanese patent application"). They have further attempted to blend surfactants with such VIP analogs to improve absorption properties, and to blend peptidase inhibitors therewith to improve stability (JP-A-5-238950).

However, the polypeptide compounds and modified polypeptide compounds disclosed in these publications demonstrate poor solution stability in high concentrations, because they have an aspartic acid residue and an asparagine residue, which are likely to undergo rearrangement reactions at the 8- and 24-positions, respectively.

Accordingly, the workers at the Applicants' company have conducted extensive studies in order to develop VIP analogs having high VIP-like physiological activities and improved stability. Specifically, they have designed and synthesized novel amino acid sequences by replacing amino acids that seem to cause the unstable properties of [Leu$^7$]-VIP-Hse (i.e., a peptide derived from VIP by replacing the amino acid reside at the 17th position to Leu and adding Hse at the C-terminus) with stable ones occurring in nature, and have examined the stabilities and activities of the products in solutions. As a result, they have successfully discovered that the new VIP analogs have highly improved storage stabilities and extremely high activities (JP-A-6-220090 corresponding to EP-A-0,613,904).

Besides being easily degraded in the respiratory tract, the use of VIP is also disadvantageous because it must be repeatedly administered in large doses to achieve a sufficient medical effect and, further, because it is hardly absorbed via the respiratory tract mucosa due to its high molecular weight.

Accordingly, an object of the present invention is to provide a modified polypeptide compound that is designed to have excellent stability in vivo and persistent action, by chemically modifying the VIP analogs disclosed in the above-mentioned JP-A-6-220090 corresponding to EP-A-0, 613,904, which are superior to conventional VIP analogs in stability in an aqueous solution and in VIP-like activities.

SUMMARY OF THE INVENTION

The present inventors have conducted extensive studies in order to achieve the above-mentioned object. As a result, they have succeeded in the synthesis of a novel modified polypeptide compound of a structure represented by the following formula (I), which has VIP-like activities, by site-specifically introducing a hydrocarbon or a polyalkylamine into the polypeptide analog described in JP-A-6-220090 corresponding to EP-A-0,613,904 as cited above, via an amide linkage at the C-terminal thereof. Further, they have found that this compound suffers from no change in its pharmacological activities even after being administered into the respiratory tract, prolongs the duration of smooth muscle relaxant activity, and is excellent in its affinity for biomembranes, thus completing the present invention.

Accordingly, the present invention provides a modified polypeptide compound having the following formula (I):

Formula (I) ((SEQ ID NO: 2)-X):
His—Ser—Asp—Ala—Val—Phe—Thr—Gly—Asn—Tyr—
Thr—Lys—Leu—Arg—Lys—Gln—Leu—Ala—Ala—Lys—
Tyr—Leu—$R^1$—Lys—Ala—Leu—$R^2$—Hse—X wherein $R^1$ is selected from the group consisting of an Asn, Lys and Gln residue, $R^2$ is a Lys or Arg residue, Hse is a homoserine residue, X is $NHR^3$ or $NR^4R^5$, wherein $R^3$ is a hydrocarbon residue having 18 or less carbon atoms or a polyalkylamine having 2 or more amino groups, or $R^4$ and $R^5$ are hydrocarbon residues, provided that the total carbon number of $R^4$ and $R^5$ is 18 or less.

The present invention also provides the aforementioned modified polypeptide compound wherein $R^1$ is Asn and $R^2$ is Lys; the aforementioned modified polypeptide compound wherein $R^3$ is a member selected from the group consisting of n-propylamide, n-hexylamide, lauryloamide, stearylamide, oleylamide, dihexylamide, triethylenetetraminemonoamide, and ethylenediaminemonoamide; and the aforementioned modified polypeptide compound wherein $R^1$ is Asn, $R^2$ is Lys, and $R^3$ is a member selected from the group consisting of n-propylamide, n-hexylamide, lauryloamide, stearylamide, oleylamide, dihexylamide, triethylenetetraminemonoamide, and ethylenediaminemonoamide.

In addition, the present provides a pharmaceutical composition for preventing and treating bronchial asthma and impotence comprising as an active ingredient a pharmaceutically effective amount of at least one modified polypeptide compound mentioned above and a pharmaceutically acceptable carrier.

DETAILED DESCRIPTION OF THE INVENTION

The hydrocarbon residue of $R^3$ has 1 to 18 carbon atoms, preferably 3 to 18 carbon atoms, more preferably 6 to 12 carbon atoms.

The polyalkylamine of $R^3$ has 2 to 18 carbon atoms, preferably 4 to 18 carbon atoms, more preferably 4 to 12 carbon atoms, and also has 2 to 10 nitrogen atoms, preferably 3 to 10 nitrogen atoms, more preferably 3 to 7 nitrogen atoms.

The hydrocarbon residues of $R^4$ and $R^5$ may be the same or different and have 2 to 18 carbon atoms, preferably 3 to 18 carbon atoms, more preferably 6 to 12 carbon atoms, as the total number of carbon atoms.

The modified polypeptide of the present invention can be administered to humans or animals by, for example, inhalation for treatment of asthma or by percutaneous application for treatment of impotence, generally, in an amount of from about 1 mg/kg to 10 mg/kg per day. The modified polypeptide can be formulated into various dose forms suitable for the route of administration with a pharmaceutically acceptable carrier and using a commonly employed method of preparation. Typical but non-limiting dose forms include aerosols, powders, liquids, and ointments. Examples of the pharmaceutically acceptable carrier include soybean lecithin, citric acid, benzalkonium chloride, petrolatum, plastibase, and white beeswax.

To further illustrate the present invention in greater detail, the following Referential Production Example, Production Examples, Biological Activity Test Example, and Stability Test Example are provided.

Reference Production Example (Synthesis of the basic VIP analog)

The VIP analog having the following amino acid sequence (SEQ ID NO: 3):

(SEQ ID NO: 3):
His—Ser—Asp—Ala—Val—Phe—Thr—Gly—Asn—Tyr—
Thr—Lys—Leu—Arg—Lys—Gln—Leu—Ala—Ala—Lys—
Lys—Tyr—Leu—Asn—Lys—Ala—Leu—Lys—Hse which is disclosed in JP-A-6-220090, corresponding to EP-A-0,613,904, as described above, was synthesized with the use of a Peptide Synthesizer "Model 431A", which is a product of Applied Biosystems Co.

This polypeptide was synthesized and purified in accordance with the method disclosed in the above-mentioned JP-A-6-220090, corresponding to EP-A-0,613,904. That is, the polypeptide was synthesized by starting with N-Boc-O-benzyl-L-homoseryl- 4-(oxymethyl)phenylacetic acid, which provides homoserine (Hse) at the C-terminal of a peptide after peptide synthesis followed by removal of a protective group and removal of a resin as an insoluble carrier in a conventional manner. The peptide synthesis was carried out using a Peptide Synthesizer "Model 431A" manufactured by Applied Biosystems Co. and a commercially available aminomethylated polystyrene•HCl resin as an insoluble carrier.

The protective group was removed from the resulting peptide in accordance with a trifluoromethanesulfonic acid method as described, for example, in H. Yajima et al., *Chem. Pharm. Bull.*, vol. 23, pp. 371–373 (1975), and the peptide was separated from the resin. The resulting peptide was purified by high performance liquid chromatography (HPLC) under the following conditions.

Column: "µ-BONDASPHERE C-18" column (19 mm×15 cm) manufactured by Waters Co.

Eluent: 0.012N HCl containing acetonitrile at a linear gradient concentration of from 15% to 50%

Flow rate: 7.0 ml/min×35 min

The main peak fractions of HPLC were collected and lyophilized. The purified polypeptide thus obtained had a homoserine lactone residue at the C-terminal.

Production Example 1

(Synthesis of VIP analog-n-propylamide derivative)

10 mg of the VIP analog (SEQ ID NO: 3) obtained in the above Reference Production Example was weighed and dissolved in 0.4 ml of methanol in a glass vial. To the solution was added 75 µl of n-propylamine, and the resulting solution was reacted at 40° C. for 2 hours. Then, the reaction mixture was concentrated under reduced pressure to thereby remove the n-propylamine and the methanol. The residue was purified by HPLC with the use of a µ-BONDASPHERE C-18 column, which is manufactured by Waters Co. (19 mm×15 cm), under the following conditions:

Eluent: 0,012N hydrochloric acid containing acetonitrile at a linear gradient concentration from 15 to 36 % acetonitrile, for 40 min Flow rate: 7.0 ml/min Detection wavelength: 210 nm The major peak fraction of HPLC was collected and freeze dried. By this process, 6 mg of the targeted VIP analog-n-propylamide derivative was obtained.

The polypeptide derivative thus obtained was identified by FAB-MS under the following conditions. Analysis conditions:

Matrix: glycerol-thioglycerol (1:1 (w/w))
Inlet selection: direct
Ion mode: FAB⁺ and the following FAB-MS analytical data was obtained.

| FAB-MS analytical data (M + H)⁺: | 3348.9 (found) |
|---|---|
| | 3348.8 (anal. calcd.) |

Thus, it was confirmed that this product had a structure represented by the following formula ((SEQ ID NO: 3)-n-propylamide).

(SEQ ID NO: 3)-n-propylamide:
His—Ser—Asp—Ala—Val—Phe—Thr—Gly—Asn—Tyr—
Thr—Lys—Leu—Arg—Lys—Gln—Leu—Ala—Ala—Lys—
Lys—Tyr—Leu—Asn—lys—Ala—Leu—Lys—Hse—NH—
$(CH_2)_2CH_3$ Production Example 2

(Synthesis of VIP analog-n-hexylamide derivative)

15 mg of the VIP analog (SEQ ID NO: 3) obtained in the above Reference Production Example was weighed and dissolved in 2.3 ml of methanol in a glass vial. To the solution was added 225 µl of n-hexylamine, and the resulting solution was reacted at 40° C. for 30 minutes. Then the reaction mixture was concentrated under reduced pressure to thereby remove the methanol. The residue was purified by HPLC as specified below with the use of a µ-BONDASPHERE C-18 column, which is manufactured by Waters Co. (19 mm×15 cm), under the following conditions.

Eluent: 0.012N hydrochloric acid containing acetonitrile at a linear gradient concentration from 15 to 50% acetonitrile, for 40 min Flow rate: 7.0 ml/min Detection wavelength: 210 nm The major peak fraction of HPLC was collected and freeze dried. By this process, 7.5 mg of the targeted VIP analog-n-hexylamide derivative was obtained.

The polypeptide derivative thus obtained was identified by FAB-MS under the matrix, inlet selection and ion mode conditions as specified in the above Production Example 1 and the following FAB-MS analytical data was obtained.

| FAB-MS analytical data (M + H)⁺: | 3390.9 (found) |
|---|---|
| | 3390.9 (anal. calcd.) |

Thus, it was confirmed that this product had a structure represented by the following formula ((SEQ ID NO: 3)-n-hexylamide).

(SEQ ID NO: 3)-n-hexylamide:
His—Ser—Asp—Ala—Val—Phe—Thr—Gly—Asn—Tyr—
Thr—Lys—Leu—Arg—Lys—Gln—Leu—Ala—Ala—Lys—
Lys—Tyr—Leu—Asn—Lys—Ala—Leu—Lys—Hse—NH—
$(CH_2)_5CH_3$ Production Example 3

(Synthesis of VIP analog-laurylamide derivative)

15 mg of the VIP analog (SEQ ID NO: 3) obtained in the above Reference Production Example was weighed and dissolved in 2.3 ml of methanol in a glass vial. To the solution was added 252 mg of laurylamine, and the resulting solution was reacted at 40° C. for 1.5 hours. After completion of this reaction, 10 ml of purified water was added thereto and the excessive laurylamine was removed by extracting with chloroform. Then, the aqueous layer thus obtained was concentrated under reduced pressure and the residue was purified by HPLC under conditions specified above in Production Example 2 with the use of a µ-BONDASPHERE C-18 column, which is manufactured by Waters Co. (19 mm×15 cm).

The major peak fraction of HPLC was collected and freeze dried. By this process, 9.0 mg of the targeted VIP analog-laurylamide derivative was obtained.

The polypeptide derivative thus obtained was identified by FAB-MS under the matrix, inlet selection and ion mode conditions as specified in the above Production Example 1 and the following FAB-MS analytical data was obtained.

| FAB-MS analytical data (M + H)⁺: | 3474.9 (found) |
|---|---|
| | 3375.1 (anal. calcd.) |

Thus, it was confirmed that this product had a structure represented by the following formula ((SEQ ID NO: 3)-laurylamide).

(SEQ ID NO: 3)-n-laurylamide:
His—Ser—Asp—Ala—Val—Phe—Thr—Gly—Asn—Tyr—
Thr—Lys—Leu—Arg—Lys—Gln—Leu—Ala—Ala—Lys—
Lys—Tyr—Leu—Asn—Lys—Ala—Leu—Lys—Hse—NH—
$(CH_2)_{11}CH_3$ Production Example 4

(Synthesis of VIP analog-stearylamide derivative)

15 mg of the VIP analog (SEQ ID NO: 3) obtained in the above Reference Production Example was weighed and dissolved in 4.5 ml of methanol in a glass vial. To the solution was added 367 mg of stearylamine, and the resulting solution was reacted at 40° C. for 30 minutes. After completion of the reaction, 10 ml of purified water was added thereto and excess stearylamine was removed by extracting with chloroform. Then, the aqueous layer thus obtained was concentrated under reduced pressure and the residue was purified by HPLC with the use of a µ-BONDASPHERE C-18 column, which is manufactured by Waters Co. (19 mm×15 cm), under the following conditions.

Eluent: 0.012N hydrochloric acid containing acetonitrile at a linear concentration from 30 to 50% acetonitrile, for 35 min Flow rate: 7.0 ml/min Detection wavelength: 210 nm The major peak fraction of HPLC was collected and freeze dried. By this process, 10.2 mg of the targeted VIP analog-stearylamide derivative was obtained.

The polypeptide derivative thus obtained was identified by FAB-MS under the matrix, inlet selection and ion mode conditions as specified in the above Production Example 1 and the following FAB-MS analytical data was obtained.

| FAB-MS analytical data (M + H)⁺: | 3359.1 (found) |
|---|---|
| | 3359.2 (anal. calcd.) |

Thus, it was confirmed that this product had a structure represented by the following formula ((SEQ ID NO: 3)-stearylamide).

(SEQ ID NO: 3)-n-stearylamide:

-continued

His—Ser—Asp—Ala—Val—Phe—Thr—Gly—Asn—Tyr—
Thr—Lys—Leu—Arg—Lys—Gln—Leu—Ala—Ala—Lys—
Lys—Tyr—Leu—Asn—Lys—Ala—Leu—Lys—Hse—NH—
$(CH_2)_{17}CH_3$

Production Example 5

(Synthesis of VIP analog-oleylamide derivative)

15 mg of the VIP analog (SEQ ID NO: 3) obtained in the above Reference Production Example was weighed and dissolved in 4.5 ml of methanol in a glass vial. To the solution was added 365 mg of oleylamine, and the resulting solution was reacted at 45° C. for 30 minutes. After completion of the reaction, 10 ml of purified water was added thereto and excess oleylamine was removed by extracting with chloroform. Then, the aqueous layer thus obtained was concentrated under reduced pressure and the residue was purified by HPLC under the conditions as specified in the above Production Example 4 with the use of a μ-BONDA-SPHERE C-18 column, which is manufactured by Waters Co. (19 mm×15 cm).

The major peak fraction of HPLC was collected and freeze dried. By this process, 13.4 mg of the targeted VIP analog-oleylamide derivative was obtained.

The polypeptide derivative thus obtained was identified by FAB-MS under the matrix, inlet selection and ion mode conditions as specified in the above Production Example 1 and the following FAB-MS analytical data was obtained.

| FAB-MS analytical data $(M + H)^+$: | 3556.1 (found) |
|---|---|
| | 3556.3 (anal. calcd.) |

Thus, it was confirmed that this product had a structure represented by the following formula ((SEQ ID NO: 3)-oleylamide).

(SEQ ID NO: 3)-n-oleylamide:
His—Ser—Asp—Ala—Val—Phe—Thr—Gly—Asn—Tyr—
Thr—Lys—Leu—Arg—Lys—Gln—Leu—Ala—Ala—Lys—
Lys—Tyr—Leu—Asn—Lys—Ala—Leu—Lys—Hse—NH—
$(CH_2)_8CH=CH(CH_2)_7CH_3$

Production Example 6

(Synthesis of VIP analog-dihexylamide derivative)

10 mg of the VIP analog (SEQ ID NO: 3) obtained in the above Reference Production Example was weighed and dissolved in 1.0 ml of methanol in a glass vial. To the solution was added 211 μl of dihexylamine, and the resulting solution was reacted at 45° C. for 1 hour. After completion of the reaction, 5 ml of purified water was added thereto and excess dihexylamine was removed by extracting with chloroform. Then, the aqueous layer thus obtained was freeze-dried and purified by HPLC under the conditions as specified in the above Production Example 2 with the use of a μ-BONDASPHERE C-18 column, which is manufactured by Waters Co. (19 mm×15 cm).

The major peak fraction of HPLC was collected and freeze dried. By this process, 6.8 mg of the targeted VIP analog-dihexylamide derivative was obtained.

The polypeptide derivative thus obtained was identified by FAB-MS under the matrix, inlet selection and ion mode conditions as specified in the above Production Example 1 and the following FAB-MS analytical data was obtained.

| FAB-MS analytical data $(M + H)^+$: | 3474.3 (found) |
|---|---|
| | 3474.1 (anal. calcd.) |

Thus, it was confirmed that this product had a structure represented by the following formula ((SEQ ID NO: 3)-dihexylamide).

(SEQ ID NO: 3)-n-dihexylamide:
His—Ser—Asp—Ala—Val—Phe—Thr—Gly—Asn—Tyr—
Thr—Lys—Leu—Arg—Lys—Gln—Leu—Ala—Ala—Lys—
Lys—Tyr—Leu—Asn—Lys—Ala—Leu—Lys—Hse—NH—
$[(CH_2)_5CH_3]_2$

Production Example 7

(Synthesis of VIP analog-triethylenetetraminemonoamide derivative)

8.0 mg of the VIP (SEQ ID NO: 3) analog obtained in the above Reference Production Example was weighed and dissolved in 0.8 ml of methanol in a glass vial. To the solution was added 109 μl of triethylenetetramine, and the resulting solution was reacted at 40° C. for 30 minutes. Then, the reaction mixture was purified by HPLC under the conditions as specified in the above Production Example 2.

The major peak fraction of HPLC was collected and freeze dried. By this process, 5.7 mg of the targeted VIP analog-triethylenetetraminemonoamide derivative was obtained. The polypeptide derivative thus obtained was identified by FAB-MS under the matrix, inlet selection and ion mode conditions as specified in the above Production Example 1 and the following FAB-MS analytical data was obtained.

| FAB-MS analytical data $(M + H)^+$: | 3435.2 (found) |
|---|---|
| | 3435.0 (anal. calcd.) |

Thus, it was confirmed that this product had a structure represented by the following formula ((SEQ ID NO: 3)-triethylenetetraminemonoamide).

(SEQ ID NO: 3)-n-triethylenetetraminemonoamide:
His—Ser—Asp—Ala—Val—Phe—Thr—Gly—Asn—Tyr—
Thr—Lys—Leu—Arg—Lys—Gln—Leu—Ala—Ala—Lys—
Lys—Tyr—Leu—Asn—Lys—Ala—Leu—Lys—Hse—NH—
$[(CH_2)_2NH]_3H$

Production Example 8

(Synthesis of VIP analog-ethylenediaminemonoamide derivative)

10 mg of the VIP analog (SEQ ID NO: 3) obtained in the above Reference Production Example was weighed and dissolved in 1.0 ml of methanol in a glass vial. To the solution was added 50 μl of ethylenediamine, and the resulting solution was reacted at 40° C. for 30 minutes. Then, the reaction mixture was purified by HPLC under the conditions as specified in the above Production Example 2.

The major peak fraction of HPLC was collected and freeze dried. By this process, 7.7 mg of the targeted VIP analog-ethylenediaminemonoamide derivative was obtained.

The polypeptide derivative thus obtained was identified by FAB-MS under the matrix, inlet selection and ion mode conditions as specified in the above Production Example 1 and the following FAB-MS analytical data was obtained.

FAB-MS analytical data (M + H)+: 3348.9 (found)
3349.1 (anal. calcd.)

Thus, it was confirmed that this product had a structure represented by the following formula ((SEQ ID NO: 3)-ethylenediaminemonoamide).

(SEQ ID NO: 3)-n-ethylenediaminemonoamide:
His—Ser—Asp—Ala—Val—Phe—Thr—Gly—Asn—Tyr—
Thr—Lys—Leu—Arg—Lys—Gln—Leu—Ala—Ala—Lys—
Lys—Tyr—Leu—Asn—Lys—Ala—Leu—Lys—Hse—NH—
(CH$_2$)$_2$NH$_2$ Test Example 1

(Measurement of elution time in reversed phase HPLC)

It is well known that the elution time in HPLC with the use of a reversed phase column correlates to the hydrophobicity of a compound (cf. *J. Med. Chem.*, vol. 18, pp. 549–552 (1975) and *J. Pharm. Sci.*, vol. 66, pp. 747–749 (1977)). Thus, the elution time of each of the VIP analog derivatives obtained in the above Reference Production Example and production Examples was measured under the HPLC conditions as specified below. As a control, natural VIP having a human type amino acid sequence (purchased from Peptide Institute, INC.) was employed.

Column: μ-BONDASPHERE C-18 column (manufactured by Millipore Corporation, 3.9 mm×150 mm)

Column temp.: 40° C.

Eluent: eluted with 0.012N hydrochloric containing 15, 25 and 50% of acetonitrile in this order, for 50 minutes Flow rate: 0.8 ml/min Detection wavelength: 210 nm The results obtained are shown in Table 1 below. Thus, it has been shown that the elution time is prolonged when a hydrocarbon residue exists at the C-terminal, which increases the chain length, and that the elution time is shortened when a hydrophilic polyamine is added thereto.

TABLE 1

| Sample | Retention time (min) |
| --- | --- |
| VIP | 23.9 |
| Reference Production Example | 13.8 |
| Production Example 1 | 18.0 |
| Production Example 2 | 24.2 |
| Production Example 3 | 40.0 |
| Production Example 4 | 46.8 |
| Production Example 5 | 48.3 |
| Production Example 6 | 41.4 |
| Production Example 7 | 10.9 |
| Production Example 8 | 12.1 |

Test Example 2

(Comparison of stability in a broncho-alveolar lavage wash)

Natural type VIP and the VIP analog derivative obtained in the above Production Example 2 ((SEQ ID NO: 3)-n-hexylamide) were examined for their stability in a broncho-alveolar lavage wash. First, male Hartley guinea pigs (weight: 350–380 g) were anesthetized by intraperitoneally administering urethane. Next, the respiratory tract of each animal was exposed by cutting its neck and 4 ml of physiological saline was slowly injected into the respiratory tract. Then, the injected solution was recovered from the respiratory tract, which is referred to as the broncho-alveolar lavage wash.

33 μg of (SEQ ID NO: 3)-n-hexylamide obtained in Production Example 2 or the natural type VIP described in Test Example 1 was weighed, added to 0.1 ml of the broncho-alveolar lavage wash, which had been adjusted to pH 7.8 with a Tris-HCl buffer solution, and incubated at 37° C. 1, 2, 3 and 4 hours after the initiation of the incubation, the reaction mixture was collected and the residual concentration of the (SEQ ID NO: 3)-n-hexylamide or the natural type VIP was measure under the following HPLC conditions to thereby determine the half-life thereof.

Column: μ-BONDASPHERE C-18 column (manufactured Waters Co., 3.9 mm×150 mm)

Column temp.: 40° C.

Eluent: eluted with 0.012N hydrochloric containing acetonitrile at a linear gradient concentration from 15 to 25%, for 20 min Flow rate: 0.8 ml/min Detection wavelength: 210 nm As a result, the half-life of the natural type VIP was 1.2 hours, whereas that of the (SEQ ID NO: 3)-n-hexylamide was 4.9 hours. Thus, it has been shown that half life of the degradation of this modified polypeptide compound is significantly prolonged in the broncho-alveolar lavage wash.

Test Example 3

(Duration of bronchoconstriction suppressing activity)

The inhibitory activity of the VIP analog derivatives, obtained in the Production Examples above, on histamine-induced bronchoconstriction was evaluated on test samples in accordance with a Konzett-Rössler method. Natural type VIP was used as a control.

First, a male guinea pig was fixed under urethane-anesthesia. After cutting the neck of the animal, a canula drug line was inserted into its jugular vein while a canula connected to a Konzett-Rössler device was inserted into its respiratory tract. After dropping a test drug directly into the respiratory tract, the head of the animal was held up for 1 minute to allow the drug to reach the lungs. Subsequently, 5 μg/kg of histamine was intravenously administered to the animal and the bronchoconstriction was measured over time. One minute before the administration of histamine, succinylcholine chloride was intravenously administered to the animal to thereby suppress spontaneous respiration during the experiment. Evaluation was made in the following manner. Before the administration of the test drug, the intensity of bronchoconstriction induced by histamine was measured. Then, after the administration of the test drug, the time required for reducing by 50% the suppression of bronchoconstriction induced by the same dose of histamine as measured above was defined as $t_{50}$. The $t_{50}$ of each test drug was determined. Table 2 shows the results. Compared to the natural type VIP employed as the control, each of the VIP analog derivatives obtained in the above Production Examples showed a significant increase (p<0.05) in $t_{50}$, which indicates that the duration of the bronchoconstriction suppressing activity was prolonged.

TABLE 2

| Sample | $t_{50}$ (min) |
| --- | --- |
| Natural VIP | 6 |

TABLE 2-continued

| Sample | $t_{50}$ (min) |
|---|---|
| Reference Production Example | 26 |
| Production Example 2 | 60 |
| Production Example 3 | 61 |
| Production Example 7 | 58 |

Compared with natural type VIP, the modified polypeptide compound according to the present invention has several elevated biological activities, for example, it acts as an enhanced smooth muscle relaxant, it has an extremely high stability, and can prolong the duration of the suppression of bronchoconstriction by about 10 times. Accordingly, the modified polypeptide compound of the present invention is superior to the publicly known natural type VIP in regard to its applicability as a drug.

Among the modified polypeptide compounds of the present invention, those having a lipophilic residue at the C-terminal have high affinities for biomembranes and are excellent in stability and duration of action.

On the other hand, those having a polyamine at the C-terminal undergo electrostatic bindings to acidic lipids on the surface of cells. Thus, these compounds provide excellent retention and stability at the administration site when administered by, for example, inhalation.

Accordingly, the above-mentioned modified polypeptide compounds of the present invention can be used as an active ingredient in drugs for preventing and treating asthma and impotence, and is effective even in a small dose.

While the invention has been described in detail and with reference to specific examples thereof, it will be apparent to one skilled in the art that various changes and modifications can be made therein without departing from the spirit and scope thereof.

What is claimed is:

1. A polypeptide compound having the following general formula ((SEQ ID NO: 2)-X):

His—Ser—Asp—Ala—Val—Phe—Thr—Gly—Asn—Tyr—
Thr—Lys—Leu—Arg—Lys—Gln—Leu—Ala—Ala—Lys—
Lys—Tyr—Leu—$R^1$—Lys—Ala—Leu—$R^2$—Hse—X— wherein $R^1$ is selected from the group consisting of an Asn, Lys and Gln residue, $R^2$ is a Lys or Arg residue, Hse is a homoserine residue, and X is $NHR^3$ or $NR_4R^5$, wherein $R^3$ is a hydrocarbon residue having 18 or less carbon atoms or a polyalkylamine having 2 or more amino groups in its molecule, and $R^4$ and $R^5$ are hydrocarbon residues, provided that the total carbon number of $R^4$ and $R^5$ is 18 or less.

2. The polypeptide compound of claim 1, wherein $R^1$ is Asn and $R^2$ is Lys.

3. The polypeptide compound of claim 1, wherein $R^3$ is selected from the group consisting of n-propylamide, n-hexylamide, lauryloamide, stearylamide, oleylamide, dihexylamide, triethylenetetraminemonoamide, and ethylenediaminemonoamide.

4. The polypeptide compound of claim 1, wherein $R^1$ is Asn, $R^2$ is Lys, and $R^3$ is selected from the group consisting of n-propylamide, n-hexylamide, lauryloamide, stearylamide, oleylamide, dihexylamide, triethylenetetraminemonoamide, and ethylenediaminemonoamide.

5. A pharmaceutical composition comprising as an active ingredient a pharmaceutically effective amount of at least one polypeptide compound having the following general formula ((SEQ ID NO: 2)-X):

His—Ser—Asp—Ala—Val—Phe—Thr—Gly—Asn—Tyr—
Thr—Lys—Leu—Arg—Lys—Gln—Leu—Ala—Ala—Lys—
Lys—Tyr—Leu—$R^1$—Lys—Ala—Leu—$R^2$—Hse—X wherein $R^1$ is selected from the group consisting of an Asn, Lys and Gln residue, $R^2$ is a Lys or Arg residue, Hse is a homoserine residue, and X is $NHR^3$ or $NR^4R^5$, wherein $R^3$ is a hydrocarbon residue having 18 or less carbon atoms or a polyalkylamine having 2 or more amino groups in its molecule, and $R^4$ and $R^5$ are hydrocarbon residues, provided that the total carbon number of $R^4$ and $R^5$ is 18 or less, and a pharmaceutically acceptable carrier.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
His  Ser  Asp  Ala  Val  Phe  Thr  Asp  Asn  Tyr  Thr  Arg  Leu  Arg  Lys  Gln
1                   5                        10                            15

Met  Ala  Val  Lys  Lys  Tyr  Leu  Asn  Ser  Ile  Leu  Asn
                20                       25
```

( 2 ) INFORMATION FOR SEQ ID NO:2:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
His  Ser  Asp  Ala  Val  Phe  Thr  Gly  Asn  Tyr  Thr  Lys  Leu  Arg  Lys  Gln
1                   5                        10                            15

Leu  Ala  Ala  Lys  Lys  Tyr  Leu  Xaa  Lys  Ala  Leu  Xaa  Xaa
                20                       25
```

( 2 ) INFORMATION FOR SEQ ID NO:3:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear (ii) MOLECULE TYPE: peptide (xi) SEQUENCE DESCRIPTION: SEQ ID NO:3:

His Ser Asp Ala Val Phe Thr Gly Asn Tyr Thr Lys Leu Arg Lys Gln
1               5                   10                  15
Leu Ala Ala Lys Tyr Leu Asn Lys Ala Leu Lys Xaa
            20                  25